United States Patent [19]

Ripa et al.

[11] Patent Number: 5,599,931
[45] Date of Patent: Feb. 4, 1997

[54] PROCESS FOR SEPARATING STEREOISOMERS OF FOLINIC ACID

[75] Inventors: Giorgio Ripa; Rodolfo Piva, both of Milan, Italy; Ernst Fekder, Riva S. Vitale, Switzerland

[73] Assignee: Bracco S.p.A., Milan, Italy

[21] Appl. No.: 456,767

[22] Filed: Jun. 1, 1995

Related U.S. Application Data

[63] Continuation of Ser. No. 290,812, Aug. 17, 1994, abandoned.

[30] Foreign Application Priority Data

Feb. 20, 1992 [IT] Italy .................. MI92A0367

[51] Int. Cl.$^6$ .................................................. C07D 475/04
[52] U.S. Cl. ................................................. 544/258
[58] Field of Search .................................... 544/258

[56] References Cited

U.S. PATENT DOCUMENTS

| | | | |
|---|---|---|---|
| 2,688,018 | 8/1954 | Cosulich | 544/258 |
| 4,206,307 | 6/1980 | Temple | 544/258 |
| 4,500,711 | 2/1985 | Wisowaty et al. | 544/258 |
| 5,010,194 | 4/1991 | Mueller et al. | 544/258 |
| 5,134,235 | 7/1992 | Mueller et al. | 544/258 |
| 5,194,611 | 3/1993 | Marazza et al. | 544/258 |
| 5,239,078 | 8/1993 | Marazza et al. | 544/247 |
| 5,350,850 | 9/1994 | Vecchi | 544/258 |
| 5,391,738 | 2/1995 | Vecchi | 544/258 |

FOREIGN PATENT DOCUMENTS

| | | |
|---|---|---|
| 93-15076 | 8/1993 | WIPO . |
| 93-17022 | 9/1993 | WIPO . |

*Primary Examiner*—Donald G. Daus
*Attorney, Agent, or Firm*—Bucknam and Archer

[57] ABSTRACT

The (6S) stereoisomer of folinic acid is obtained in high optical purity by salification of (R,S) folinic acid with di- or polyamines and subsequent selective crystallization of the desired diasteromeric salt.

11 Claims, No Drawings

PROCESS FOR SEPARATING STEREOISOMERS OF FOLINIC ACID

This is a continuation of application Ser. No. 08/290,812, filed Aug. 17, 1994, now abandoned.

The present invention relates to a process for separating stereoisomers of folinic acid.

Folinic acid, i.e. N-(5-formyl-(6R,S)-5,6,7,8-tetrahydropteroyl)-L-glutamic acid, when obtained by chemical synthesis, is formed by an equimolar mixture of its two (6R) and (6S) diastereomeric forms.

It is known that only the (6S) isomer, as calcium salt, has the well-known pharmacological activity of the product, while the other one is totally devoid of it. Therefore, there is a strong need for a process allowing the preparation of the optically pure (6S) form.

Various attempts were made to synthetize (6S) isomer through asymmetrical synthesis but they were not fully successful from the industrial point of view.

As far as the separation of both diastereomers from their equimolar mixture is concerned, it is worth citing U.S. Pat. No. 2,688,018 and patent application WO 88/03844, even if they have not yet provided the ideal solution to the problem.

It has now been found a process allowing the separation and the isolation with good yields of the two optically pure (6R) and (6S) forms of folinic acid, both free and salified with alkaline-earth metal ions, from the equimolar diastereomeric mixture produced by chemical synthesis starting from folic acid.

Another remarkable embodiment of this invention relates to a process for the preparation and isolation of salt derivatives of (6R)-folinic acid, respectively (6S)-folinic acid, characterised by an excellent optical purity (O.P.), with suitable at least dibasic organic amines, which are aliphatic, straight, cyclic and/or heterocyclic, from said diastereomeric equimolar mixture.

Another remarkable embodiment of this invention is represented by the new salts of (6R)-folinic and/or (6S)-folinic acid with said amines.

Folinic acid is usually prepared by synthesis starting from folic acid, which contains a (S) chiral centre in that part of the molecule corresponding to (S)-glutamic acid. By hydrogenating the double bond between the 5- and 6- positions of the pterinic residue, a new chiral centre in the 6- position is originated with a (6R,S) configuration. The subsequent formylation step of nitrogen atom at the 5-position leads to the production of (6R,S)-folinic acid.

It now has been surprisingly found that, by crystallization of (6R,S)-folinic acid salts with at least dibasic organic amines from a suitable solvent or preferably, from binary or ternary mixtures of solvents, mixtures of said salts enriched in their (6R) or (6S) form can be obtained, according to the amines used.

Said optically enriched mixtures can be further enriched in the preponderant isomeric form through one or more recrystallizations to obtain the corresponding salts with said amines of (6R)-folinic acid, respectively (6S)-folinic acid, with an O.P. of at least 99%, usually higher than 99%.

The conversion from these salts to the corresponding salts with alkaline-earth metal ions with the same optical purity is very easy.

By way of example, from the mixture enriched in its (6S)-form, the calcium salt (or the corresponding salts with alkaline-earth metal ions) of (6S)-folinic acid can be prepared with an O.P. higher than 99%. This result can preferably be achieved according to one of the following methods:

a) from the aqueous solution of the (6S) enriched diamino folinate, through treatment with an alkaline-earth metal chloride at neutral pH and optionally in presence of a precipitating solvent, the alkaline-earth metal salt of the (6S) enriched folinic acid is separated. Further crystallizations from a suitable solvent or solvent mixtures lead to the optically pure (6S) form of the desired alkaline-earth metal folinate, b) the (6S) enriched diamino folinate is recrystallized from suitable solvent mixtures in order to obtain the optically pure (6S) form. The corresponding salt with alkaline-earth metal ions is subsequently obtained through exchange, as described in a).

The same process can be applied to the (6R) enriched mixture to obtain the corresponding (6R) isomer with an O.P. higher than 99%.

Preferred metal cations to salify (6R,S)-folinic acid and its optically pure diastereomeric forms are those of the alkaline-earth metals, especially Ca, Mg, St, Ba. $Ca^{2+}$ ion is particularly preferred.

At least dibasic organic amines suitable for the salification of (6R,S)-folinic acid can be selected from straight, cyclic or heterocyclic, substituted or unsubstituted, racemic or chiral, aliphatic di- or polyamines, which contain at least two amino groups linked to one another by at least one substituted or unsubstituted hydrocarbon chain, comprising at least 2 or 3 C atoms.

Particularly preferred amines are diamines of general formulae from I to III,

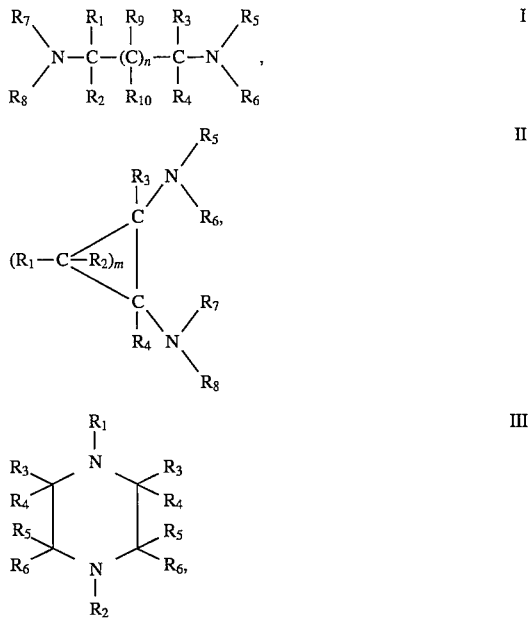

wherein:

$R_1$ to $R_8$ which are the same or different, are H or straight or branched $C_{1-6}$ alkyl groups, which can be substituted by 1–4 OH groups and/or by 1–4 alkoxy or hydroxyalkoxy groups, $R_9$ to $R_{10}$ which are the same or different, are $R_1$ or OH, n 0–6, m 2–8.

By way of non-limiting example, particularly preferred diamines can be selected from: ethylenediamine, 1,2-diamino-propane, 1,3-diamino-propane, 1,3-diamino-2-hydroxy-propane, (cis)-1,2-diamino-cyclohexane, (trans)-1,2-diamino-cyclohexane, piperazine, 1,4-dimethyl-piperazine, 2-methyl-piperazine, 2,5-dimethyl-piperazine. Equally preferred amines can also be polyamino straight derivatives or macrocyclic compounds containing from 3 to 6N atoms.

By way of example, among these last ones, 1,4,7,10-tetraazacyclododecane and its derivatives substituted both on ethylene bridges and on nitrogen atoms can be cited.

Suitable solvents for the crystallization of diastereomeric mixtures of folinic acid salts with said amines are preferably binary or ternary water/dipolar aprotic organic solvent mixtures and/or mixtures of water/dipolar aprotic organic solvent/protic organic solvent.

Preferred protic organic solvents are, i.e., methanol, ethanol, n-propanol, isopropanol, ethylene glycol, 1,2-propylene glycol, 1,3-propylene glycol, formamide, N-methyl-formamide.

Preferred dipolar aprotic organic solvents are, i.e., dimethylformamide (DMF), dimethylacetamide (DMAC), dimethylsulphoxide (DMSO), N-methyl-pyrrolydone (NMP), hexamethylphosphoramide (HMPT).

The process of this invention is hereinafter described, employing, by way of non-limiting example as starting material the calcium salt of (6R,S)-folinic acid and it is performed according to the following steps:

STEP 1

Precipitation of (6R,S)-folinic acid from an aqueous solution of its calcium salt, by adjusting pH between 1 and 3 with mineral acids at a temperature ranging from 0° to 25° C.

STEP 2

Formation of (6R,S)-folinic acid salts with diamines/polyamines in a dipolar aprotic organic solvent, preferably DMAC. Said salts are obtained under a solid form by:

a) dissolution of (6R,S)-folinic acid in a dipolar aprotic solvent, in a weight/volume ratio ranging from 1:5 to 1:20 (w/v);

b) reaction, at a temperature from 5° to 35° C., with a stoichiometric amount, or a molar excess not higher than 20%, of the desired amine, dissolved either in the same dipolar aprotic solvent in a ratio ranging from 1:5 to 1:50 (w/v) or in a protic organic solvent in a ratio ranging from 1:5 (w/v) to 1:15 (w/v);

c) gradually cooling the reaction medium at a temperature ranging from 25° C. to 5° C., up to a complete precipitation of the desired salt. Precipitation can be facilitated by adding a protic organic solvent in a volume ratio ranging from 0.1:1 to 2:1 (v/v) compared with the dipolar aprotic solvent.

Said salification reaction can also be performed in water, in suspension phase, followed by dilution of the resulting aqueous solution with or in a water-soluble protic organic solvent, which acts as a precipitating agent.

STEP 3

Partial separation of folinic acid diastereomers by crystallization or insolubilization of its salts with said amines from a water/dipolar aprotic water-soluble solvent, optionally with addition of an organic protic solvent.

The weight/volume (w/v) ratio salt/mixtures of solvents can range from 1:2 to 1:60, preferably from 1:4 to 1:45.

The composition of the mixture water/dipolar aprotic solvent (v/v) can range from 1:0.5 to 1:20, preferably from 1:1 to 1:15; such mixture can also contain a protic organic solvent in amounts up to 70% in volume, preferably to 50%, in case said protic organic solvent is needed.

The salts of (6R,S)-folinic acid with the above mentioned amines can directly be dissolved in the desired mixture of solvents at a temperature comprised between 25° and 70° C., preferably 30° and 50° C.

On the other hand, they can also be dissolved in water. The desired amount of dipolar aprotic solvent, optionally together with the required additional amount of protic organic solvent, is subsequently added to said aqueous solution.

Then these solutions are gradually cooled to nearly 0° C. while crystallization takes place.

The obtained solid moiety consists of a mixture of (6R) and (6S) isomers of amino-folinates, which is enriched in the less soluble form (i.e. R or S, depending on the amino compound used as salifying agent).

For example, crystallization of ethylenediamino (6R,S)-folinate leads to a mixture enriched in the (6R) isomer salt.

On the contrary, from piperazino (6R,S)-folinate, the (6S) form preferably crystallizes.

Usually said enriched solid mixtures show an O.P. ranging from 65 to 98%.

Crystallization mother liquors are obviously enriched in the other isometic form and show an O.P. value usually ranging from 65 to 80%.

STEP 4

Further purification of the partially optically purified amino folinates, deriving from Step 3, is performed through one or more recrystallizations of the same from a mixture water/dipolar aprotic solvent whose composition ranges from 1:1 (v/v) to 1:20 (v/v). This crystallizing mixture can optionally contain also a protic organic solvent in amounts up to 50% in volume. The desired optically pure amino folinate is obtained with an O.P. higher than 99%.

Then said optically pure amino folinate can be transformed into the corresponding (6R), respectively (6S), calcium folinate.

One of the preferred ways consists in crystallizing said amino folinate from water (pH=7 and temperature in the range 0°–25°0 C.) in the presence of 0.2 to 5, preferably 2 to 4, parts (w/w) of water soluble calcium salts, preferably chlorides or nitrates.

Alternatively the desired optically pure calcium folinate can be precipitated from the above mentioned aqueous $Ca^{2+}$ containing solution by adding a great excess of a protic water-soluble organic solvent.

STEP 5

The stereoisomers of folinic acid, which are contained in the mother liquors resulting from the crystallizations described in Step 3, are also recovered from said mother liquors with an O.P. higher than 99%.

They can be obtained either as amino or calcium salts, preferably following one of the procedures hereinafter described.

a) From the above mentioned mother liquors the organic protic solvent, if present, is distilled off under reduced pressure at temperatures from 25° to 50° C. and subsequently the water-soluble dipolar aprotic solvent is removed by extracting the mixture with a water-insoluble organic solvent, preferably methylene chloride ($CH_2Cl_2$). To the resulting aqueous solution $CaCl_2$ is added in amounts corresponding to 0.2–5, preferably to 2–4, parts in weight (w/w) in relation with the starting quantity of amino (6R,S)-folinate. Then pH is adjusted to a value ranging between 6 and 7 by means of 1N NaOH and, by adding ethanol the precipitation of the desired calcium salt is obtained, operating at a temperature of 0°–25° C., preferably 5°–25° C.

Calcium folinate, enriched in its prevailing diastereomer, with an O.P. ranging from 65 to 85%, is recovered through filtration. The optically pure calcium folinate (O.P. higher than 99%) is finally obtained through one or more crystallizations from 10 to 100 volume of water, with pH ranging from 6 to 7 and at temperatures from 0° to 25° C.

b) To mother liquors, deriving from Step 3, suitable precipitating solvents, either dipolar aprotic or protic organic solvents, are added in amounts equal to 0.05–5 volumes in relation with the mother liquors volume. By cooling to 0°–20° C., the prevailing optical isomer of diamino folinate can be preferentially crystallized with an O.P. higher than 70%. The desired amine folinate with an O.P. higher than 99% is then obtained by one or more crystallizations from water/dipolar aprotic solvent mixtures with a ratio ranging from 1:1 to 1:20 (v/v), optionally by adding a protic organic solvent, in amounts up to 50% in volume.

Amino (6R,S)-folinate obtained as described in Steps 1 and 2 can alternatively be prepared directly from a calcium (6R,S)-folinate aqueous solution. To this solution another aqueous solution can be added containing, in stoichiometric amounts compared with the starting folinate, the desired amine salified with a mineral or organic acid which forms insoluble salts with alkaline-earth metal cations, preferably anions of sulphuric or oxalic acid. The insoluble salt precipitating, i.e. calcium oxalate, is filtered off and to the resulting aqueous solution, containing the desired diamino (6R,S)-folinate, the suitable amount of dipolar aprotic solvent is subsequently added, optionally added with protic organic solvent as previously described.

Crystallization can be performed at a temperature ranging from 0° to 25° C. and lasts from 1 h up to five days by operating at a neutral or slightly alkaline pH. The procedure described in step 1 can also be adopted in order to obtain the optically pure isomers of free folinic acid (6R or 6S), with an O.P. higher than 99%, starting from the corresponding optically pure salts of the same obtained according to step 4 and 5.

The following examples aim at better disclosing the most remarkable features of this invention, and are not a limit to the same for the skilled technician.

EXAMPLE 1

Preparation of pure (6R,S)-folinic acid.

100 g of calcium (6R,S)-folinate pentahydrate, dissolved in 750 ml of water and 670 ml of 0.5N hydrochloric acid, are added dropwise at the same time to 300 ml of water, under stirring and at 5°–20° C. Then the obtained suspension, containing (6R,S)-folinic acid, is kept under stirring for 1 h at 5°–25° C. After that the precipitate is filtered, washed with water and dried. 76 g of (6R,S)-folinic acid are obtained.

HPLC titre: ≧99% performed under the following chromatographic conditions:

Column: Hibar® Lichrosphere RP18-5 μm (Merck): 250 mm length; 4 mm diameter.

Mobile phase: A=phosphate buffer pH 7.8; B=25% methanol in phosphate buffer pH 7.8 (v/v).

Flow rate: 1.2 ml/min; column temperature: 35° C.: UV 254 nm detector.

Gradient: from 0 to 2 min B=12%, from 2 to 20 min straight gradient up to B=80% then maintenance for 3 min, then inverse gradient from 23 to 35 min up to B=12%.

Following the same procedure the following free acid compounds have been obtained:

(6E)-folinic acid with an O.P. higher than 99%, starting from calcium (6S)-folinate of Example 6.

(6R)-folinic acid with an O.P. higher than 99%, starting from ethylenediamino (6R)-folinate of Example 6.

EXAMPLE 2

Preparation of ethylenediamino (6R,S)-folinate.

75 g of (6R,S)-folinic acid are dissolved in 750 ml of dimethylacetamide (DMAC). 10.5 g of ethylenediamine, dissolved in 400 ml of the same solvent, are added at a temperature of 5°–35° C. The precipitated salt suspension is kept under stirring for abut 1 h, at 5°–25° C., then is filtered. After drying, 82 g of ethylenediamino (6R,S)-folinate are obtained.

HPLC titre: ≧98.5% according to the chromatographic method of Example 1.

EXAMPLE 3

Diastereomer separation of ethylenediamino (6R,S)-folinate.

80 g of ethylenediamino (6R,S)-folinate are dissolved in 740 ml of water. 920 ml of DMAC are added under stirring at a temperature of 25°–40° C. Then temperature is lowered to 5° C. and the product crystallizes, under stirring, for 24 h. After that the precipitate is filtered off and washed with ethanol. After drying, 40.2 g of ethylenediamino folinate are obtained, containing the 80% of (6R) diasteroisomer. The (6R) form content is determined by performing a chiral HPLC under the following conditions:

Column: length 250 mm; diameter 4 mm; manually fed with Chiral Si 300 BSA (SERVA), 5 μm stationary phase.

Mobile phase: 0.25M solution of $NaH_2PO_4$ in water.

Flow rate: 1.0 ml/min; column temperature 40° C.; detector: UV 280 nm (310 nm).

Mother liquors, after filtration, contain ethylenediamino (6S)-folinate with a 60% diastereomeric excess (determined with chiral HPLC under the above mentioned conditions).

Chromatographic conditions disclosed in Examples 1 and 3 are also used for controls and determinations in the remaining examples.

EXAMPLE 4

Ethylenediamino (6S)-folinate isolation and purification.

To the mother liquors derived from the crystallization described in Example 3 and mostly containing ethylenediamino (6S)-folinate, with a 60% diastereomeric excess, 170 ml of DMAC are added. The solution is kept under stirring for 48 h at 10° C. The resulting precipitate is filtered, washed with ethanol and dried. 15 g of ethylenediamino (6S)-folinate are obtained with an O.P. higher than 99% (chiral HPLC control was performed according to Example 3).

HPLC titre: ≧58.5; $[\alpha]^{20}_D = -14.8°$ (c=2.1% $H_2O$).

EXAMPLE 5

Preparation of calcium (6S)-folinate from ethylenediamino (6S)-folinate.

To 10 g of ethylenediamino (6S)-folinate (obtained as disclosed in Example 4), dissolved into 100 ml of water, 10 g of calcium chloride and 400 ml of ethanol are added under stirring at 5°–25° C. The separated precipitate is filtered, washed with aqueous ethanol (95%) and dried. Then, the product is dissolved again in water at pH 6–6.5, at 50°–60° C. One part in weight of calcium chloride is added and pH is adjusted to 7 with NaOH 1N. The desired compound crystallizes at 0°–25° C. for 16 h.

The precipitated crystalline product is filtered, washed with cold water and aqueous ethanol and dried. 11 g of calcium (6S)-folinate containing about 20% of crystallization water are obtained with an O.P. higher than 99% (through chiral HPLC).
MPLC titre: >99%; $[\alpha]^{20}_D = -15°(c=1\%$ $H_2O)$.

EXAMPLE 6

Purification of ethylenediamino (6R)-folinate.

35 g of ethylenediamino (6R)-folinate (obtained as described in Example 3), with 80% O.P., are recrystallized from 500 ml of water/DMAC with a volumetric ratio of 1/1.25. Temperature and crystallization time are the following: 0°–25° C. and 48 h. The crystallized product is filtered, washed with ethanol and dried. 25 g of ethylenediamino (6R)-folinate with an O.P. higher than 99% (chiral HPLC) are obtained. $[\alpha]^{20}_D = +44.4°(c=2.1\%$ $H_2O)$.

EXAMPLE 7

Calcium (6S)-folinate isolation and purification from an ethylenediamino folinate mixture enriched in the (6S) isomer.

The mother liquors deriving from the crystallization described in Example 3 and mostly containing ethylenediamino (6S)-folinate with a 60% diasteroisometic excess are extracted with 5×400 ml methylene chloride. To the resulting aqueous solution, 50 g of calcium chloride are added under stirring at 0°–25° C., then pH is adjusted to 7 with NaOH 1N and 250 ml of ethanol are added. The solid separated product is filtered, washed with aqueous ethanol and dried. The resulting product is recrystallized twice from water, at pH 7, at 0°–25° C. and in the presence of 3 parts in weight of calcium chloride and washing the filtered product every time, the first time with cold water and then with ethanol.

17 g of calcium (6S)-folinate are obtained with an O.P. higher than 99% (through chiral HPLC) and with about 20% crystallization water content.
HPLC titre: >99%; $[\alpha]^{20}_D = -15°$ $(c=1\%$ $H_2O)$.

EXAMPLE 8

Piperazino (6R,S)-folinate preparation.

80 g of (6R,S)-folinic acid, prepared as described in Example 1, are dissolved in 950 ml of DMAC. 17.5 g of piperazine dissolved into 2000 ml of ethanol are added thereto under stirring at a temperature of 5°–30° C. The resulting suspension is kept under stirring for 3 h at room temperature and then filtered. The wet product is washed with ethanol, and then dried. 90.5 g of piperazino (6R,S)-folinate are obtained.
HPLC titre: >99%.

EXAMPLE 9

Diastereomer separation of piperazino (6R,S)-folinate.

85 g of piperazino (6R,S)-folinate are suspended in 3600 ml of a mixture water/DMAC (1:10.5 v/v). Temperature is raised to 35° C., until the solid compound is completely dissolved. Crystallization takes 3 days at 5° C., under stirring. The obtained precipitate is filtered, washed with ethanol and dried. 35 g of piperazino (6S)-folinate with an O.P. of ≧97% are recovered.

EXAMPLE 10

Piperazino (6S)-folinate purification.

10 g of piperazino (6S)-folinate, obtained as described in Example 9, are recrystallized from a mixture water/DMAC (1:10.5 v/v) following the procedure of Example 6. After filtering, washing and drying the crystalline product, 8 g of piperazino (6S)-folinate with an O.P. higher than 99% (chiral HPCL control) are obtained.

EXAMPLE 11

Piperazino (6R)-folinate isolation and purification.

To the mother liquors derived from the crystallization described in Example 9, mostly containing piperazino (6R)-folinate, 1800 ml of ethanol are added. Crystallization takes place at 5° C., for 64 h. The precipitate is then filtered, washed with ethanol and dried. 30 g of piperazino (6R)-folinate, with an O.P. of ≧94% (chiral HPCL control) are recovered.

Said salt is then recrystallized from a mixture water/DMAC/ethanol (1:10:5 v/v/v), following the procedure of Example 6, to give the desired product with an O.P. higher then 99%.

EXAMPLE 12

Preparation of calcium (6S)-folinate from piperazino (6S)-folinate.

Calcium (6S)-folinate with an O.P. higher than 99% is obtained in yield of 80% from the piperazino (6S)-folinate deriving from Example 10 following the procedure described in Example 5.

EXAMPLE 13

Preparation of 1,4-dimethylpiperazino (6R,S)-folinate 80 g of (6R,S)-folinic acid, prepared as described in Example 1, are dissolved into 800 ml of DMAC. 21 g of 1,4-dimethyl-piperazine, dissolved in 460 of DMAC, are added under stirring at a temperature of 5°–25° C., then 700 ml of ethanol are added. The solution is kept under stirring for 5 days at 5° C. to obtain a precipitate which is filtered, washed with ethanol and dried.

90 g of 1,4-dimethylpiperazine (6R,S)-folinate are obtained.
(HPLC titre: >99%).

EXAMPLE 14

Preparation of 1,3-diamino-2-hydroxy-propane (6R,S)-folinate.

80 g of (6R,S)-folinic acid, prepared as described in Example 1, are dissolved into 800 ml of DMAC. 16.8 g of 1,3-diamino-2-hydroxy-propane dissolved into 420 ml of DMAC are added under stirring at 5°–25° C. The solution is kept under stirring for 1.5 h at the same temperature to obtain a precipitate which is filtered, washed first with DMAC and then with ethanol, and then dried. 89 g of 1,3-diamino-2-hydroxy-propane (6R,S)-folinate are obtained (HPLC titre >99%).

EXAMPLE 15

Partial separation of 1,3-diamino-2-hydroxy-propane (6R, S)-folinate diastereomers, 87 g of 1,3-diamino-2-hydroxy-propane ( 6R,S)-folinate are dissolved into 600 ml of water. 780 ml of DMAC are added under stirring and at a temperature of 25°–40° C. The product crystallizes at 5° C. from the solution kept under stirring for 2 days, then is filtered. The wet product is washed with ethanol. After drying, 50 g of 1,3-diamino-2-hydroxypropane folinate containing about 70% of diastereomer (6R) (chiral HPLC), are obtained. In the residual crystallization mother liquors, the (6S) diastereomer is present in about 55% diastereomeric excess.

EXAMPLE 16

1,3-diamino-2-hydroxy-propane (6S)-folinate isolation and purification.

160 ml of DMAC are added to the mother liquors deriving from the fractional crystallization described in Example 15, and containing 1,3-diamino-2-hydroxypropane (6S)-folinate, with a 55% diastereomeric excess. The solution is kept under stirring for 30 h at 5° C. to obtain a precipitate which is filtered and washed with ethanol. After drying, 20 g of 1,3-diamino-2-hydroxy-propane (6S)-folinate are obtained with 95% O.P. This product is recrystallized from 300 ml of water/DMAC mixture in a volumetric ratio of 1/1.5 at a 0°–25° C. temperature. The resulting precipitate is filtered and washed with ethanol. After drying, 16 g of 1,3-diamino-2-hydroxy-propane (6S)-folinate are obtained with an O.P. higher than 99% (determined through chiral HPLC), titre ≧98.5%.

We claim:

1. A process for the separation of the (6R) and (6S) diastereoisomers of folinic acid or the calcium salt thereof of the desired high optical purity, which comprises the steps of:

a) reacting racemic folinic acid in a liquid medium consisting of 1) water; 2) a mixture of water and a protic organic solvent which is a member selected from the group consisting of methanol, ethanol, n-propanol, isopropanol, ethylene glycol, 1,2-propylene glycol, 1,3-propylene glycol, formamide and N-methyl-formamide; 3) water, said protic organic solvent as in 2) and a dipolar aprotic organic solvent which is dimethylformamide, dimethylacetamide, dimethylsulphoxide, N-methyl-pyrrolidone or hexamethylphosphoramide; 4) dimethyl acetamide or 5) a mixture of water and dimethyl acetamide with a basic diamine, said diamine having formula I, II or III

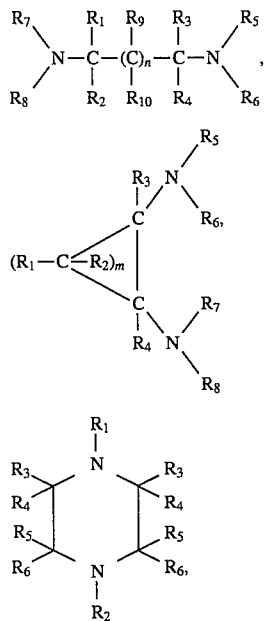

wherein:

$R_1$ to $R_8$ are the same or different, and are H or straight or branched $C_{1-6}$ alkyl groups, unsubstituted or substituted by 1–4 OH groups, 1–4 alkoxy groups or hydroxyalkoxy groups, $R_9$ and $R_{10}$ are the same or different, and are the same as $R_1$ or OH, n is 0–6, and m is 2–8;

at a temperature of 5°–35° C. followed by cooling at 25°–5° C. whereby the racemic salt of folinic acid and said diamine is obtained;

b) dissolving said racemic salt from step a) in a solvent as the solvent defined in step a) hereinabove at a temperature of 25°–70° C., followed by cooling to about 0° C. whereby the first solid which separates upon cooling contains a major portion of a first one of the said (6R) or (6S) diastereoisomers, the major portion of the other second isomer remaining in the crystallization mother-liquors;

c) purifying by recrystallization at least once the isomer-enriched solid from step b), from the same solvent used in said step b) until the first diastereoisomeric salt with said diamine is obtained in a desired optical purity, and then converting said salt with said diamine into the calcium salt and when free folinic acid as the first diastereoisomer is desired reacting said calcium salt with hydrochloric acid in water and cooling to precipitate said free folinic acid from said first diastereoisomer;

d) isolating the second diastereoisomeric salt from the mother-liquors from step b).

2. The process according to claim 1 wherein said diamine in step a) is a member selected from the group consisting of ethylenediamine, 1,2-diaminopropane, 1,3-diamino-propane, 1,3-diamino-2-hydroxy-propane, (cis)-1,2-diamino-cyclohexane, (trans)-1,2-diamino-cyclohexane, piperazine, 2-methyl-piperazine, 1,4-dimethyl-piperazine and 2,5-dimethyl-piperazine.

3. The process according to claim 2 wherein said diamine in step a) is ethylene diamine and said first diastereoisomer in step b) is the (6R) diastereoisomer.

4. The process according to claim 2 wherein said diamine in step a) is piperazine and said first diastereoisomer in step b) is the (6S) diastereoisomer.

5. The process according to claim 1 wherein in step d) said second diastereoisomer is isolated from the mother liquor from step b) by concentrating said mother liquor under vacuo at 25°–50° C. adding calcium chloride, whereby a solid calcium folinate enriched in said second diastereoisomer is obtained and recrystallizing said solid with 10–100 volumes of water at a temperature of 0°–25° C. until the desired optical purity is obtained.

6. The process according to claim 1 wherein in step d) a dipolar aprotic solvent or a protic organic solvent as defined in step a) is added, in an amount of 0.05–5 volumes based on the volume of said mother liquor, then cooling at 0°–20° C. to precipitate the second diastereoisomer of said salt of the diamino folinate with a degree of purity higher than 70%, and recrystallizing said salt at least once from a mixture of water and a dipolar aprotic solvent as defined hereinabove to achieve a degree of purity higher than 99%.

7. The process according to claim 1 wherein in said step a) the reaction is carried out with said basic diamine in a stoichiometric amount or in molar excess not higher than 20%.

8. The process according to claim 1 wherein said steps b) and c) are performed in a solvent mixture consisting of the components water and one of said water-soluble dipolar aprotic organic solvents, wherein said components range, in a volumetric ratio, from 1:0.5 (v/v) to 1:20 (v/v), or said steps are performed in a solvent containing said water/water-soluble dipolar aprotic organic solvent mixture together with one of said protic organic solvents in amounts up to 70% in volume.

9. The process according to claim 1 wherein the weight/volume ratio between said racemic diamine folinate salts and said solvent in step b), ranges from 1:2 (w/v) to 1:60 (w/v).

10. The process according to claim 1 wherein the optically pure salts of folinic acid, obtained in steps c) or d), are dissolved in water and the resulting aqueous solutions are acidified by adding a mineral acid to a pH value of 1–3 at a temperature ranging from 0° to 25° C., wherein said (6R) or (6S) diastereoisomers of folinic acid precipitate with an O.P. higher than 99%.

11. A diamino-folinate which is a member selected from the group consisting of:

Ethylenediamino (6S)-folinate;

Piperazino (6S)-folinate;

1,4-dimethyl-piperazino (6S)-folinate;

1,3-diamino-2-hydroxy-propyl (6S)-folinate.

* * * * *